United States Patent [19]
Thompson

[11] Patent Number: 5,906,615
[45] Date of Patent: May 25, 1999

[54] SERPENTINE ABLATION/COAGULATION ELECTRODE

[75] Inventor: Todd Thompson, Pleasanton, Calif.

[73] Assignee: FemRx, Inc., Calif.

[21] Appl. No.: 08/829,377

[22] Filed: Mar. 31, 1997

[51] Int. Cl.$^6$ .................................................. A61B 17/36
[52] U.S. Cl. ............................... 606/45; 606/41; 606/46; 606/49
[58] Field of Search ................................. 606/40–50, 34, 606/37

[56] References Cited

U.S. PATENT DOCUMENTS

| | | | |
|---|---|---|---|
| 3,901,242 | 8/1975 | Storz | 128/303.15 |
| 5,100,423 | 3/1992 | Fearnot | 606/159 |
| 5,192,280 | 3/1993 | Parins | 606/48 |
| 5,197,964 | 3/1993 | Parins | 606/48 |
| 5,277,201 | 1/1994 | Stern | 607/98 |
| 5,431,649 | 7/1995 | Mulier et al. | 606/41 |
| 5,507,743 | 4/1996 | Edwards et al. | 606/41 |
| 5,569,244 | 10/1996 | Hahnen | 606/46 |
| 5,582,610 | 12/1996 | Grossi et al. | 606/46 |
| 5,658,280 | 8/1997 | Issa | 606/45 |
| 5,669,906 | 9/1997 | Grossi et al. | 606/45 |
| 5,766,168 | 6/1998 | Mantell | 606/46 |

FOREIGN PATENT DOCUMENTS 0 316 995  5/1989  European Pat. Off. ......... A61N 1/05

*Primary Examiner*—Jack W. Lavinder
*Assistant Examiner*—David M. Ruddy

[57] ABSTRACT

The present invention provides devices, systems, and methods for using a single electrode structure for both resection and ablation. Generally, the electrode structures of the present invention comprise fixed wire shapes which avoid the complexity and binding that often result when known rolling ablation elements are powered to the high electrosurgical potentials required for removal of tissues. Electrosurgical energy requirements are minimized by concentrating potential at narrow cutting surfaces, and physician effort is avoided by minimizing the total profile of the device along a selected cutting axis. In the exemplary embodiment, a serpentine wire has multiple electrosurgical elements which are aligned with a low cutting profile, and which provide a large lateral surface area for simultaneous ablation of uterine and other tissues.

22 Claims, 4 Drawing Sheets

SERPENTINE ABLATION/COAGULATION ELECTRODE

BACKGROUND OF THE INVENTION

1. Field of the Invention

This invention relates generally to electrosurgical devices, and in one particular aspect, provides a serpentine electrode which is adapted for removing tissue, and for sliding over a tissue surface for ablation and/or coagulation.

Electrocautery has been in use for many years as a surgical technique. For example, it is known to use electrosurgical cutting elements in transcervical fibroid removal to sever and remove uterine tissues. Such severing of tissues requires electrical potentials at high voltage settings, typically being an alternating current of between about 100 KHz and 2.2 GHz, and between about 500 and 16,000 volts. This energy is transmitted from a small cutting surface of a surgical instrument to the tissues at the surgical site. Uterine cavity distension can facilitate this electrosurgical procedure, typically with a nonconductive fluid such as sorbitol-mannitol or the like under sufficient pressure to separate the walls of the uterus and render the surgical site suitable for optical fiber observation. The cutting surface usually consists of a wire or other solid shape, and the transmission of current to the tissue is often monopolar, with the circuit completed by a conductive pad applied to the patient's skin.

More recently, bipolar electrocautery systems and devices have been proposed for use in conductive solutions such as saline. These bipolar devices often incorporate a return path through a relatively large conductive surface near the cutting wire, so that the energy is concentrated only at the cutting surface adjacent the target tissues.

In both monopolar and bipolar systems, heat generated from the resistance of tissues to the concentrated flow of electrical current is high enough to vaporize cells near the cutting surface. Thus, a cut is made with very little physical resistance from the small cutting surface. Small diameter electrosurgical cutting wires minimize total physician effort, particularly when severing relatively large amounts of tissues. Heat from the cutting element can also cauterize smaller blood vessels, so that visibility remains reasonably good.

Electrosurgical resistance heating may also be used at much lower power densities to coagulate bleeding tissues, and to kill selected areas of tissue through ablation. Ablation/coagulation electrodes are generally much larger in surface area and cross-section than electrosurgical cutting wires. These large, specialized electrodes treat broad surfaces without penetrating the tissue. Electrosurgical ablation probes are used within the uterus to kill the endometrial lining, often using a conductive roller ball or barrel to heat a wide swath of tissue with each stroke. Once again, distention with a conductive or nonconductive medium can help expose the uterine lining.

While these differing electrosurgical methods have been largely successful, they suffer from significant disadvantages. In particular, it is often desirable to use a cutting device for resection of fibroids, and during the same procedure, to cauterize any bleeding blood vessels or to ablate alternative portions of the uterus. Generally, this requires removal of the resection wire from the distended uterus and insertion of a roller ball or roller barrel electrode. This electrode removal and replacement significantly increases the time required for each procedure, and can complicate the fluid pressurization method and system to maintain distention throughout both procedures.

It has previously been proposed to use a single electrode structure for both cutting and ablation. Unfortunately, the drag from known large ablation electrodes adds substantially to physician effort during removal of tissues. In addition, high power settings associated with vaporization and severing of tissues results in a build-up of hardened electrosurgical debris and tissue on the rolling ablation elements. This tissue and debris build-up can prevent rolling and interfere with visibility. While two different electrode structures can be included in a single probe, this adds to probe cost, complexity, and size, and may result in a less maneuverable device.

In light of the above, it would be advantageous to provide improved electrodes, electrosurgical systems, and electrosurgical methods. It would be particularly advantageous to provide enhanced structures and techniques to facilitate resection, ablation, and coagulation with a single electrode. Preferably, these improvements would minimize physician effort and avoid tissue adherence effects, but would not significantly increase complexity or cost over known electrosurgical systems.

2. Description of the Background Art

U.S. Pat. No. 5,197,964 describes a bipolar instrument having a stationary electrode and a movable electrode. U.S. Pat. No. 5,192,280 describes a pivoting multiple loop bipolar cutting device, and U.S. Pat. No. 5,528,610 describes a grooved slider electrode for a resectoscope, in which the electrode may have a number of different configurations. U.S. Pat. No. 5,277,201 describes an endometrial ablation apparatus and method. U.S. Pat. No. 5,507,743 is directed toward a coiled radio frequency electrode treatment apparatus. U.S. Pat. No. 5,100,423 describes an ablation catheter, while U.S. Pat. No. 5,431,649 describes an alternative method and apparatus for radio frequency ablation. European Patent Application No. 0,316,995 is also relevant.

SUMMARY OF THE INVENTION

The present invention provides electrodes, electrosurgical systems, and electrosurgical methods for using a single structure for resection, ablation, and coagulation. Generally, the electrode structures of the present invention comprise fixed wire shapes to avoid the binding that often results when known rolling ablation/coagulation elements are powered with the high electrosurgical potentials used for removal of tissues. Electrosurgical potential is concentrated at small profile cutting surfaces, and physician effort is avoided by minimizing the total profile of the device along a pre-determined cutting axis. In an exemplary embodiment, a serpentine electrode wire has multiple electrosurgical elements which are aligned along the cutting axis to present a small cutting profile. This simple serpentine electrode structure provides a large lateral surface area which slides easily over tissue surfaces for ablation and coagulation of uterine and other tissues.

In a first aspect, the present invention provides an electrosurgical device comprising an electrosurgical cutting element having a cutting surface. At least one electrosurgical ablation element is separated from and substantially disposed behind the cutting surface of the cutting element to minimize drag when translated through tissue toward the cutting surface. Each ablation element has an ablation surface, and a combined ablation surface, including each of the ablation surfaces, is larger than the cutting surface and oriented to slide concurrently over a tissue surface.

In another aspect, the invention provides an electrosurgical probe. The probe comprises a shaft having a proximal end, a distal end, and an axis therebetween. A serpentine electrosurgical wire is disposed near the distal end of the shaft. The wire defines a plurality of laterally oriented arches which are coupled in series. The arches are aligned substantially axially to avoid drag when the electrosurgical wire is energized with a cutting energy and the arches are translated through tissue. The arches each have a radially outwardly oriented surface, and these outer surfaces are aligned so as to slide over a tissue surface when the electrosurgical wire is energized with an ablation or coagulation energy.

In yet another aspect, the present invention provides an electrosurgical system comprising an electrosurgical potential source and an electrode. The potential source is capable of selectively supplying an ablation/coagulation energy and a tissue removal energy. The electrode is couplable to the potential source, and includes a plurality of wire segments which are aligned along an axis. This alignment avoids drag when the potential source energizes the wire segments with the tissue removal energy, and the energized wire segments are translated through tissue along the alignment axis. The wire segments also each have a lateral ablation surface. The ablation surfaces are aligned for simultaneously sliding over a tissue surface when the wire segments are energized with the ablation/coagulation energy.

In yet another aspect, the present invention provides an electrosurgical device comprising a primary electrosurgical wire having a length and a cross-section. The primary wire defines an arch, and a secondary electrosurgical wire is wound over at least a portion of the length of the primary wire along the arch. The secondary wire has a helical shape, and an inner diameter of the helix is substantially equal to the diameter of the primary wire, so that the secondary wire is affixed to the primary wire.

The present invention also provides an electrosurgical method. The method comprises energizing an electrosurgical structure with a high electrosurgical potential, and translating the highly energized structure through tissue. The electrosurgical structure is also energized with a moderate electrosurgical potential which is less than the high electrosurgical potential. This moderately energized structure is then slid along a surface of a tissue to raise a tissue temperature. Hence, the method makes use of a single electrode for both removal and hyperthermia of tissues, the structure ideally comprising either the serpentine or helically wound fixed electrode structures described herein.

BRIEF DESCRIPTIONS OF THE DRAWINGS

Figure 1:
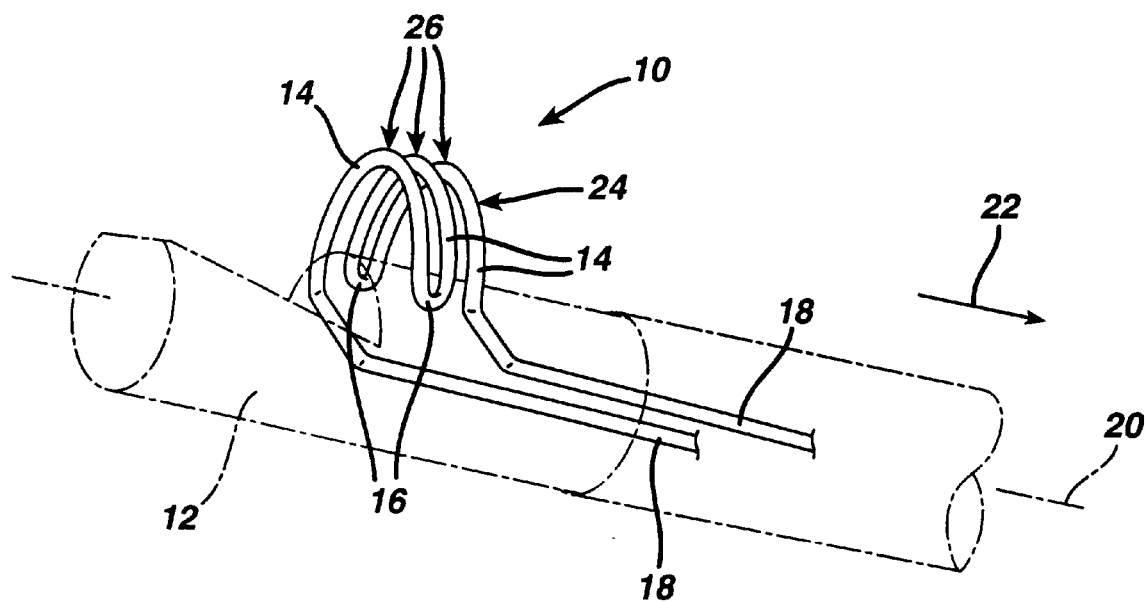
FIG. 1 is a perspective view of a serpentine electrosurgical wire which defines three arches connected in series for selectively severing tissues axially, and for laterally engaging and ablating or coagulating large tissue surfaces, according to the principles of the present invention.
Figure 3A:
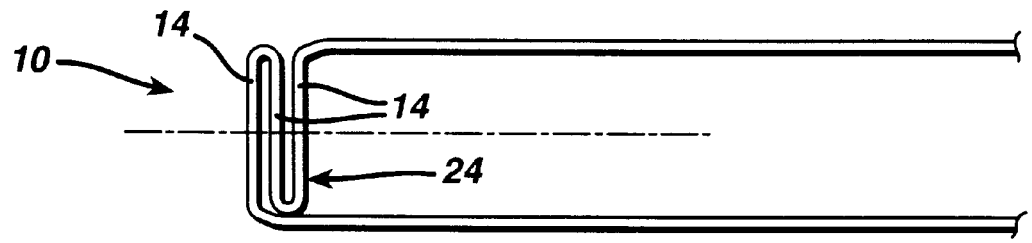
Figure 3B:
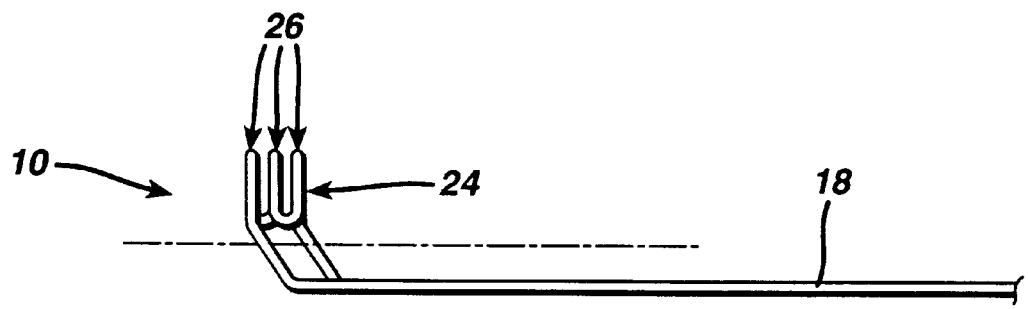
Figure 3C:
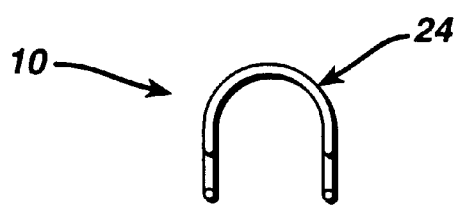

FIGS. 3A–C are top, side, and rear views of the serpentine electrosurgical wire of FIG. 1 showing the relatively large combined ablation/coagulation surface area, and the small axial cutting profile.

Figure 4:
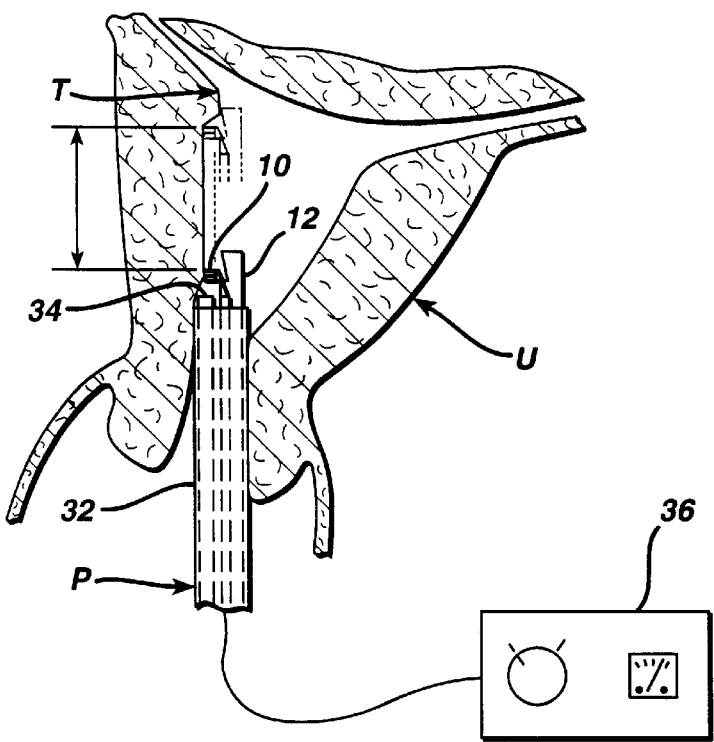

FIG. 4 is a schematic view of a system for electrosurgically removing and ablating tissues using the serpentine electrosurgical wire of FIG. 1, and also shows a method for removal and subsequent coagulation or ablation of the endometrial lining of the uterus.

Figure 5:
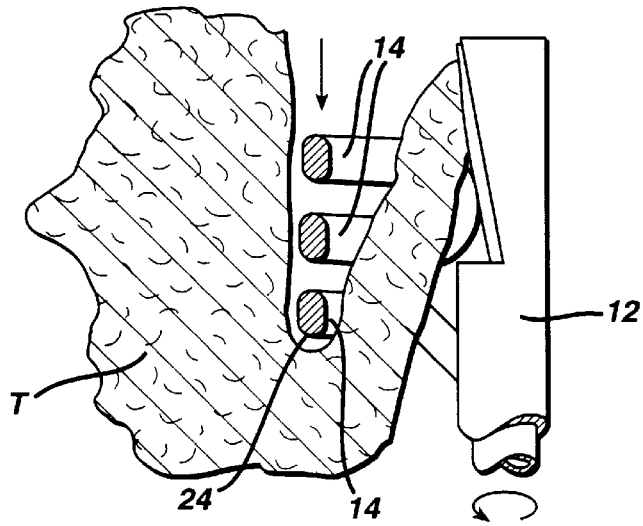

FIG. 5 is a detail view, in partial cross-section, of a method for removing tissue using the serpentine electrosurgical wire of FIG. 1.

Figure 6:
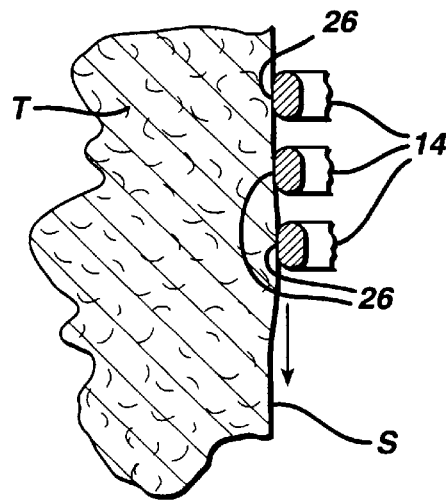

FIG. 6 is a detail view, in partial cross-section, of a method for ablating or coagulating a tissue surface using the serpentine electrosurgical wire of FIG. 1.

Figure 7:
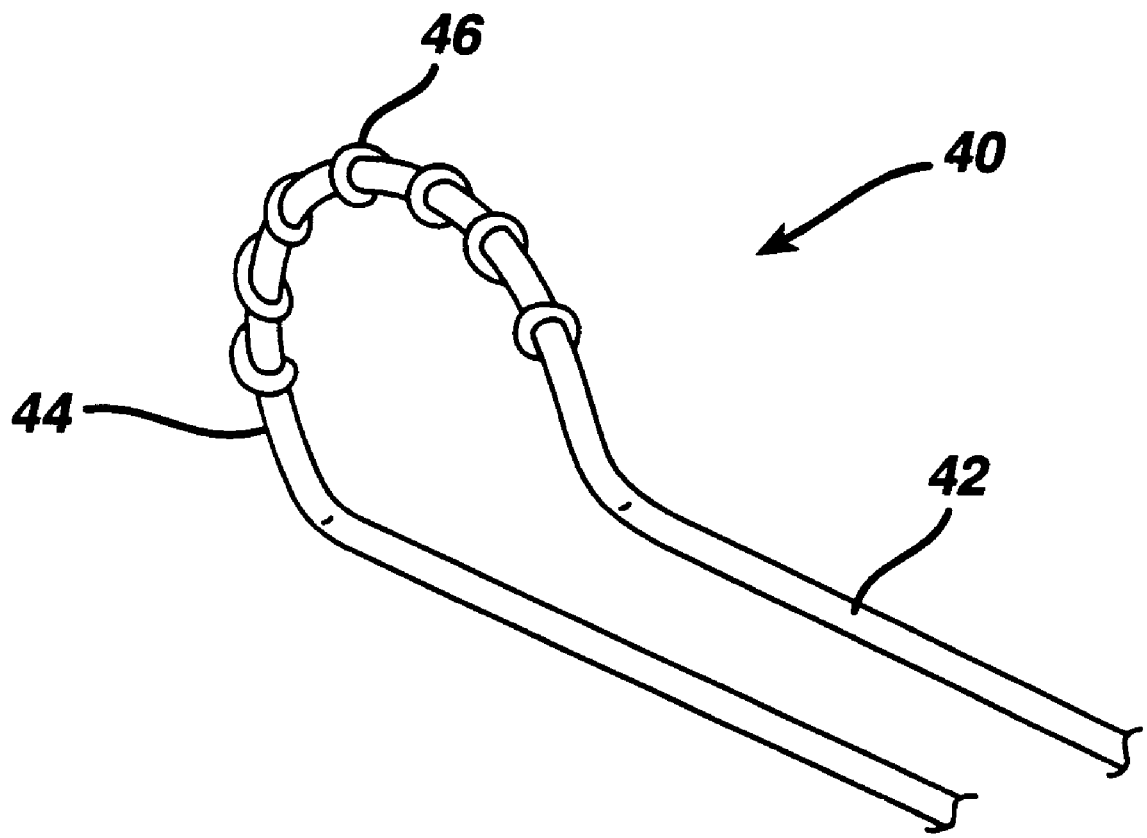

FIG. 7 is a perspective view of an alternative electrode having a primary electrosurgical wire which defines an arch, and having a secondary electrosurgical wire in the form of a helix wrapped over the arch to concentrate electrosurgical potential and reduce physician effort when the arch is translated through tissue.

DETAILED DESCRIPTIONS OF THE SPECIFIC EMBODIMENTS

The electrosurgical devices, systems, and methods of the present invention facilitate the removal, cauterization, and ablation of tissues during minimally invasive and open surgical procedures with a simple fixed electrode structure. The present invention allows the physician to utilize a single electrode for these different uses by varying the electrosurgical potential and the method of manipulation of this compact structure. Thus, the physician may make use of the varying capabilities of these electrodes without removal and replacement of multiple devices at the surgical site, providing a significant advantage over known structures, particularly for minimally invasive surgical procedures which make use of a gaseous or liquid distension medium. Hence, these methods and devices will have advantageous applications in a wide variety of thoracic and urogenital procedures, including therapies and removal of tissues of the lung, tissues of the bladder, and tissues of the prostate. The most immediate application for the present invention will be for the removal, coagulation, and ablation of the tissues lining the uterus.

Referring now to FIG. 1, a serpentine electrosurgical wire 10 is affixed to an exemplary morcellator probe shaft 12 (shown in phantom). Serpentine wire 10 defines three arches 14 which are coupled in series by bends 16. At least one of arms 18 extends proximally along the probe shaft for coupling to an electrosurgical power unit.

Arches 14 are aligned with an axis of the probe 20. This minimizes the profile of the serpentine wire when the wire is energized with a high electrosurgical potential and translated axially, preferably being translated in a proximal direction as shown by arrow 22.

When serpentine wire 10 is translated proximally, arches 14 are aligned behind a cutting surface 24. Thus, cutting is substantially entirely affected by the most proximal arch, and the distal arches add very little to the total effort required to translate the device through the tissue.

When serpentine wire 10 is energized with a more moderate electrosurgical potential, arches 14 may all be used to ablate tissues by translating the shaft laterally and engaging serpentine wire 10 against a tissue surface. Radially outwardly facing ablation surfaces 26 of the arches 14 can then slide simultaneously over the tissue surface to engage and ablate a relatively large area.

Figure 2:
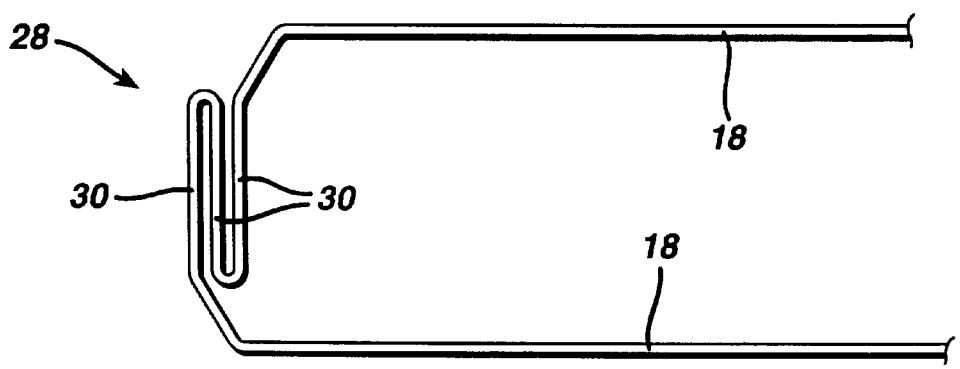
FIG. 2 is a flat pattern of the serpentine electrosurgical wire of FIG. 1, prior to the imposition of the arch radii.

A method for fabricating serpentine wire 10 can be understood with reference to FIG. 2. A flat serpentine pattern 28 is formed by bending a wire so as to define a series of aligned wire segments 30. These wire segments can then have a radius, or some other arch geometry imposed to produce the serpentine wire shape as shown in FIG. 1.

The wire will typically be metallic, preferably including a high temperature metal or alloy such as tungsten, titanium, or the like. In some embodiments, the wire will initially have a round cross-section, but will be flattened to decrease the radius of the cutting edge and increase the area of the ablation surfaces, typically after the wire is bent to form flat pattern 28 and prior to imposition of the arch radii. The final shape of serpentine wire 10 can be seen in top view, side view, and front view in FIGS. 3A, 3B, and 3C, respectively. The combined ablation surface area provided by the three independent ablation surfaces 26 is substantially larger than the surface area of cutting surface 24. The small axial profile of serpentine wire 10 is seen most clearly in the rear view shown in FIG. 3C.

An exemplary system and method for using serpentine wire 10 can be understood with reference to FIGS. 4 through 6. As is more fully explained in co-pending U.S. patent application Ser. No. 08/542,289, filed Oct. 12, 1995, (Attorney Docket No. 16944-000130), the full disclosure of which is incorporated herein by reference, visibility during electrosurgical resection can be enhanced by flowing irrigation fluid distally through an outer sheath 32 over a distally oriented scope 34. To prevent accumulation of electrosurgical debris at an internal surgical site, fluid and severed tissue is entrained within morcellating shaft 12. Morcellating shaft 12 includes an outer tubular surgical cutter having an aperture and an inner member which rotates therein to shear tissue fragments which enter the aperture. Thus, morcellating shaft 12 reduces the size of tissue for removal from an internal surgical site, significantly increasing the amount of tissue which can be removed through a given lumen size. Outer sheath 32 largely defines the outer surface of a probe P. This probe allows a visual direction of tissue removal and ablation using serpentine wire 10, and also provides an integrated irrigation and aspiration flow for removal of fluids and tissues, all within a single, compact package.

In an exemplary method of using serpentine wire 10, sheath 32 is inserted transcervically to a uterus U while an obturator is disposed in the sheath. The obturator is removed, scope 34, serpentine wire 10, and morcellating shaft 12 are advanced through positioned sheath 32, and irrigation fluid flows through the outer sheath to distend the uterus. The irrigation fluid comprises a clear fluid such as sorbitol-mannitol, mannitol, glycine, saline, or the like.

Serpentine wire 10 is energized using an electrosurgical power unit 36. Power unit 36 selectably energizes serpentine wire 10 with a tissue removal electrosurgical energy or a tissue ablation electrosurgical energy. Generally, wire 10 will be selectably energized with between about 10 and 300 watts. For removal of tissues, serpentine wire 10 will typically be energized with an electrical potential providing a total of about 150 watts. When used for ablation and/or coagulation of tissue surfaces, power unit 36 will typically provide a total energy of about 80 watts.

Tissue removal will be optically directed using scope 34 while serpentine wire 10 is energized with a tissue removal potential. In some embodiments, serpentine wire 10 and morcellating shaft 12 will move axially independently from sheath 32, and the energized serpentine wire will be drawn proximally through a tissue T toward a substantially fixed scope 34 and sheath 32. In other embodiments, the scope, serpentine wire 10, and morcellating shaft 12 will all be drawn proximally together. Regardless, arches 14 translate through tissue T behind cutting surface 24, as can be understood with reference to FIG. 5. Hence, despite the relatively large total surface area of arches 14, the drag on serpentine wire 10 is quite small. Ideally, cutting surface 24 defines a relatively small diameter which concentrates electrosurgical energy and vaporizes the adjacent tissue. The tissue is severed in strips, which are then drawn into morcellating shaft 12 with the aspiration flow. The morcellator shears the tissue strips into fragments and removes the tissue fragments and aspiration fluid proximally through probe P.

After removal of a target tissue, serpentine wire 10 can be used to coagulate any bleeding blood vessels and/or ablate tissues adjoining the newly formed tissue surface. Potential source 36 energizes serpentine wire 10 with the more moderate ablation potential, and the serpentine wire is then manipulated laterally against a surface S of tissue T so that ablation surfaces 26 of arches 14 engage the tissue surface. Ablation surfaces 26 slide simultaneously over tissue surface S without removing significant tissue. However, the potential difference between the tissue and serpentine wire heats the tissue adjacent surface S. In some embodiments, the impedance between serpentine wire 10 and the engaged tissue is used in a feedback control system to vary the electrosurgical potential and control the depth and temperature of tissue heating. Such feedback may also be used to control tissue removal potentials.

Referring now to FIG. 7, an alternative ablation/removal electrode 40 includes a primary electrosurgical element 42 which defines an arch 44. A secondary helical electrosurgical element 46 is wrapped over some or all of arch 44, and is affixed in position. Helical element 46 increases the overall electrode diameter and surface area, while the uneven combined surface concentrates power density sufficiently to initiate resection when high, tissue removal electrosurgical potentials are applied. Helical element 46 does not have to roll relative to the primary element 42, so that trapping of tissues and electrosurgical debris is minimized.

While the exemplary embodiments of the present invention have been described in some detail by way of illustration and for clarity, a wide variety of modifications, alternatives, and changes will be obvious to those who skill in the art. Therefore, the scope of the present invention is limited solely by the appended claims.

What is claimed is:

1. An electrosurgical device comprising:
   an electrosurgical cutting arch having a cutting surface; and
   at least one electrosurgical ablation arch which is coupled in electrical series with the electrosurgical cutting arch and is separated from and substantially disposed behind the cutting surface of the cutting arch so as to minimize drag when translated through tissue toward the cutting surface, said at least one ablation arch having an ablation surface,
   wherein a combined ablation surface of the device, includes said ablation surface, which is larger than the cutting surface and is oriented to slide concurrently over a tissue surface.

2. A device as claimed in claim 1, wherein the cutting arch and said at least one ablation arch are aligned along a cutting axis, wherein the cutting arch comprises a wire which includes an ablation surface, and wherein an axially oriented surface of the wire defines the cutting surface and a laterally oriented surface of the wire defines the ablation surface.

3. A device as claimed in claim 1, wherein a continuous wire defines the cutting arch and the at least one ablation arch.

4. A device as claimed in claim 1 further comprising a plurality of ablation arches, wherein a continuous wire defines the cutting arch and the plurality of ablation arches, wherein the ablation arches and the cutting arch are electrically coupled by bends in the wire.

5. A device as claimed in claim 1, wherein there are a plurality of the ablation elements.

6. A device as claimed in claim 1, wherein the electrode comprises a serpentine electrosurgical wire disposed near the distal end of the shaft.

7. An electrosurgical probe comprising:

a shaft having a proximal end, a distal end, and an axis therebetween; and a serpentine electrosurgical wire disposed near the distal end of the shaft, the wire defining a plurality of laterally oriented arches coupled in electrical series, the arches aligned substantially axially to avoid drag when the electrosurgical wire is energized with a tissue removal energy and the arches are translated through tissue, the arches each having a radially outwardly oriented surface, the outer surfaces of the arches being substantially aligned so as to slide concurrently over a tissue surface when the electrosurgical wire is energized with an ablation energy.

8. An electrosurgical system comprising:

an electrosurgical potential source capable of selectively supplying an ablation/coagulation energy and a tissue removal energy; and an electrosurgical device couplable to the potential source, the electrosurgical device including a plurality of wire segments coupled in electrical series that define a lateral surface area which is aligned axially along an axis of the device to avoid drag when the potential source energizes the wire segments with the tissue removal energy and the wire segments are translated through tissue along the axis, the wire segments each having a laterally oriented ablation surface, the ablation surfaces being aligned for simultaneous sliding over a tissue surface when the wire segments are energized with the ablation/coagulation energy.

9. An electrosurgical device comprising:

a primary electrosurgical wire having a length and a cross-section, the primary wire defining an arch; and a secondary electrosurgical wire wound over at least a portion of the length of the primary wire along the arch, the secondary wire having a helical shape, an inner diameter of the helix being substantially equal to the diameter of the primary wire, the secondary wire being immovably affixed to the primary wire.

10. An electrosurgical method comprising:

energizing an electrosurgical structure with a high electrosurgical potential, wherein the structure has a cutting element coupled in electrical series with an ablation/coagulation element;

translating the highly energized structure through tissue to remove a target tissue;

energizing the electrosurgical structure with a moderate electrosurgical potential which is less than the high electrosurgical potential; and sliding the moderately energized structure along a surface of a tissue to raise a tissue temperature.

11. A method as claimed in claim 10, wherein the electrosurgical structure comprises a serpentine wire which defines a plurality of arches aligned along a cutting axis, and wherein the arches are translated though the tissue along the cutting axis behind a cutting surface of one of the arches.

12. A method as claimed in claim 11, further comprising simultaneously sliding at least one ablation surface on said arches along the tissue surface during the translation step.

13. A method as claimed in claim 10, further comprising concentrating the electrosurgical potential at a cutting surface, the cutting surface having an arched geometry.

14. A method as claimed in claim 13, further comprising concentrating the electrosurgical potential with a secondary wire coiled and affixed over a primary electrosurgical wire of the structure.

15. An electrosurgical device comprising:

a shaft having a proximal end, a distal end, and an axis therebetween; and an electrode located near the distal end of the shaft, said electrode having a cutting surface and an ablation/coagulation surface spaced apart from the cutting surface, wherein the electrode comprises a wire defining a plurality of lateral arches coupled in electrical series and aligned along said axis between said proximal end and said distal end.

16. A device as claimed in claim 15, wherein an axially oriented surface of the wire defines the cutting surface and a laterally oriented surface of the wire defines the ablation/coagulation surface.

17. A device as claimed in claim 16 wherein the cutting surface is located on a first wire segment and the ablation/coagulation surface is located on a second wire segment.

18. An electrosurgical method comprising:

energizing an electrosurgical structure with a high electrosurgical potential, said structure having at least three arches coupled in electrical series;

translating the highly energized structure through tissue to remove a target tissue;

energizing the electrosurgical structure with a moderate electrosurgical potential which is less than the high electrosurgical potential; and sliding the moderately energized structure along a surface of a tissue to raise a tissue temperature.

19. A method as claimed in claim 18, wherein the electrosurgical structure comprises a serpentine wire wherein said arches are translated though the tissue along the cutting axis behind a cutting surface of one of the arches.

20. A method as claimed in claim 19, further comprising simultaneously sliding a plurality of ablation/coagulation surfaces on said arches along the tissue surface during said translation step.

21. A method as claimed in claim 19, further comprising concentrating the electrosurgical potential at a cutting surface, the cutting surface having an arch geometry.

22. A method as claimed in claim 19 wherein a plurality of ablation/coagulation surfaces are located on an outer circumferential surface of said arches.

* * * * *